US006299873B1

(12) United States Patent
Smilowitz et al.

(10) Patent No.: US 6,299,873 B1
(45) Date of Patent: Oct. 9, 2001

(54) METHOD FOR IMPROVEMENT OF RADIATION THERAPY OF MALIGNANT TUMORS

(75) Inventors: Henry M. Smilowitz, West Hartford, CT (US); Jeffrey A. Coderre, Wading River; Daniel N. Slatkin, Southold, both of NY (US)

(73) Assignee: University of Connecticut, Farmington, CT (US)

( * ) Notice: Subject to any disclaimer, the term of this patent is extended or adjusted under 35 U.S.C. 154(b) by 0 days.

(21) Appl. No.: 09/334,312

(22) Filed: Jun. 16, 1999

Related U.S. Application Data

(60) Provisional application No. 60/089,597, filed on Jun. 17, 1998.

(51) Int. Cl.$^7$ .......................... A61K 35/00; A61K 48/00; A61K 35/12; C12N 15/85; C12N 15/63
(52) U.S. Cl. .................... 424/93.7; 424/93.2; 424/155.1; 424/93.1; 435/320.1; 435/325; 514/44; 514/64; 250/269.6
(58) Field of Search ......................... 250/269.6; 424/93.1, 424/93.2, 155.1, 93.7; 435/320.1, 325; 514/44, 64

(56) References Cited

U.S. PATENT DOCUMENTS 5,484,596 * 1/1996 Hanna et al. ..................... 424/277.1

OTHER PUBLICATIONS

Wiseman et al. Western Journal of Medicine. 151(3): 283–288, Sep. 1989.*
Hatanaka et al. Acta Neurochirurgica. 42: 57–72, 1978.*
Agrawal, S. TIBTECH. 14: 376–387, Sep. 1989.*
Chanana et al. Neurosurgery. 44(6): 1182–1193, Jun. 1999.*
Peng et al. Tumor Targeting, 4: 3–11, 1999.*
Miller et al. FASEB J. 9: 190–199, Sep. 1989.*
Barth R, Soloway AH: "Boron neutron capture therapy of brain tumors—current status and future therapy", *J. Neuro–Oncol.* 33:3–7, 1997.
Morris GM, Coderre, JA, Hopewell, JW: "Evaluation of CNS toxicity to BNCT type irradiation using a rat spinal cord model", vol. II, *Chemistry and Biology*, Eds. B. Larsson et al, Elsevier, pp 665–669, 1997.
Coderre JA, Morris GM: "The Radiation Biology of Boron Neutron–Capture Therapy", *Rad. Research*, 151, p. 1–18, 1999.
Joel DD, Slatkin DN, Fairchild RG, Micca P, Nawrocky MM: "Pharmacokinetics and tissue distribution of the sulfhydryl boranes (monomer and dimer) in glioma–bearing rats", *Strahlenther. Onkol.* 165: 167–170, 1989.
Coderre JA, Makar MS, Micca PL, Nawrocky MM, Liu HB, Joel DD, Slatkin DN, Amols: HI: "Derivations of relative biological effectiveness for the high–LET radiations produced during boron neutron capture irradiations of the 9L rat gliosarcoma in vitro and in vivo" *Int. J. Radiat. Oncol. Biol. Phys.* 27:1121, 1993.
Joel DD, Fairchild RG, Laissue JA, Saraf SK, Kalef–Ezra JA, Slatkin DN: "Boron neutron capture therapy of intracerebral rat gliosarcomas", *Proc. Natl. Acad. Sci. USA* 87:9808–9812, 1990.

* cited by examiner

*Primary Examiner*—Scott D. Priebe
*Assistant Examiner*—Anne Marie S. Beckerleg
(74) *Attorney, Agent, or Firm*—Alix, Yale & Ristas, LLP

(57) ABSTRACT

A method of optimizing malignancy therapy includes surgical removal or reduction of the body burden of malignant cells and retention of some of those cells for subsequent use in immunotherapy. Boron neutron-capture therapy is employed at a radiation dosage below the threshold for normal tissue necrosis to provide preservation of normal tissue structure. Normal tissue tolerable limits are in the range of 10–13 GY-Eq. The removed tumor cells are altered by radiation or genetically to render them incapable of unlimited clonogenic propagation and then reinjected using multiple sequenced injections.

5 Claims, 2 Drawing Sheets

METHOD FOR IMPROVEMENT OF RADIATION THERAPY OF MALIGNANT TUMORS

RELATED APPLICATION

This application is based on and claims the benefit under 35 U.S.C. §119(e) of U.S. Provisional Application No. 60/089,597 filed Jun. 17, 1998.

FIELD OF THE INVENTION

The present invention relates generally to a new method for the improvement of radiation therapy of malignant tumors.

BACKGROUND OF THE INVENTION

Typically, a patient with a malignant tumor undergoes preliminary therapy to greatly reduce the body burden of the malignant cells. This is conventionally accomplished by surgery. Depending on the clinical circumstances and on the type of malignancy, radiation therapy ("radiotherapy") may be implemented after surgery or, less commonly, before surgery or even without surgery. Radiotherapy is conventionally accomplished using high-energy ionizing photons, typically gamma radiation with energies measured in the millions of electron volts. It has been noted there is an inadequacy of post-operative radiotherapy of the most common malignant brain tumors in humans, mainly glioblastoma multiforme. Conventional photon therapy generally mandates delivery of as much radiation to the tumor as can be physically delivered, subject to the limitation that vital organs and tissues in and around the tumor that are in the path of one or several of the convergent photon beams receive doses that are below their thresholds for causing clinical dysfunction or for causing acute or delayed radiation-induced necrosis. Unfortunately, this standard of dosimetry for conventional radiation therapy does not take into account thresholds for damage to the function or integrity of cells and tissues of the immune system that may be in the path of the gamma beams. (R. Barth, _Journal of Neuro-Oncology_, 1997.) Radiation therapy alone is often effective in slowing the growth of malignant tumors, but is usually incapable of preventing devastating recurrence for much longer than one year of deeply infiltrating growth of some types of malignancies, such as the most common primary malignant brain tumor, glioblastoma multiforme. Therapies for these recurrent tumors are generally palliative for only a few months before death occurs. If one attempts to use standard radiation therapy to kill individual clonogenic tumor cells several centimeters beyond the macroscopic periphery of the tumor, whether at its first occurrence or at its recurrence, such a large dose of radiation would be needed that normal brain structure and/or function would be compromised to some unacceptable degree. For example, long term (i.e., two years or more) survivors of glioblastoma multiforme frequently have profound neurological deficiencies attributed in part to the aggressive doses of radiation used to attain such long survivals. Nevertheless, it is known in the arts of therapeutics that even well tolerated doses of standard radiation therapy do help to reduce the burden of brain tumor cells remaining after primary surgical extirpation (i.e., debulking) of the malignancy.

The present art of radiation therapy of cancer uses standards for technique and dose that are unrelated to consideration of the function of the patient's immune system except in two circumstances: 1. where the therapy employs whole-body radiation; and 2. where partial or whole-body radiation follows or precedes chemotherapy. There is no method of radiation therapy used at present that requires that the patient's immune system be specifically modified and stimulated before or after radiotherapy, and that the radiotherapy be timed or given in dose levels that conform to the requirements of that stimulation.

Also, it is known that certain adjunct therapies, implemented after primary therapies, are useful in delaying and/or mitigating the regrowth of the cancer. Adjunct therapies known to be effective are chemotherapy, including antimitotic therapy and anti-angiogenesis therapy, additional radiation and further surgical removal or partial removal of the cancer.

To date, adjunct cancer therapies based on gene therapy or immunotherapy are often characterized by insufficiency of clinical relevance and/or of realism in preclinical experimentation. A variety of therapies dependent on the genetic modification of cells have been proposed. Some of them are being tested in clinical trials. To date, none has shown to be sufficiently efficacious to warrant widespread adoption for common malignancies of the brain. Although in vitro tumor cell death can often be demonstrated, transfection of an appropriate number of specific target tumor cells in patients is usually unattainable. There is no delivery system perfected that allows delivery of the gene used in therapy into all the tumor cells. Further, animal experiments are often designed to show proof of principle rather than control of large, imminently lethal, clinically analogous tumor models. For example, the experimental tumor can be far too small relative to the experimental animal organ under study to infer clinical relevance because of the lack of correlation in scale with the size of human tumors (at the time of clinical treatment) relative to the size of the human organ and/or organism. Additionally, in some instances, experimental immunotherapy or gene therapy is implemented at an inappropriate time, e.g., before the animal has time to manifest clinical symptoms; or after tumor cells, modified in vitro, are transplanted to the test animals. The elimination of such tumors may be of scientific importance without necessarily having practical clinical relevance. We define a clinically relevant brain tumor "imminently lethal", for example, to be one that is so advanced such that the residual life span of the untreated concomitant controls will be no more than one third of total time between tumor inoculation and death from local tumor overgrowth in the brain. For example, the untreated 9L gliosarcoma causes death about three weeks after initiation. Clinically relevant experimental therapy is not begun until fourteen days after tumor inoculation. Antiangiogenesis therapies, based mainly on the pioneering work of Dr. Judah Folkman and his colleagues, are at too early a stage of clinical investigation to be evaluated in the context of this invention. However, any of these innovative therapies that proves successful clinically is likely to augment rather than degrade the effectiveness of the improvement in radiation therapy taught in this invention.

SUMMARY OF THE INVENTION

The present invention combines the advantageous characteristics of these adjunct therapies while reducing or obviating such deficiencies as are indicated above. It involves a method of combining two disparate techniques, radiation therapy and immunotherapy or gene-modified immunotherapy (also called immunoprophylaxis when the treated malignancy is microscopic), with or without other adjunct therapies, to effect a clinically useful synergy that would not exist if the two above-named modalities were implemented independently or if only one of these two modalities were implemented. Critical to this synergy is the implementation of extensive in vitro culture and, if appropriate, genetic transformation of the tumor cells during the interval between the first neurosurgical debulking and the implementation of radiation therapy.

Advantages resulting from the combination therapy of the present invention are augmented by significant (unconventional) reduction in the length of time required for the primary radiation therapy. While conventional primary radiotherapy is implemented in small fractions daily over a period of several weeks (often six weeks), peripheral tumor nest cells are growing. In its preferred embodiment, this invention prescribes use of a radiation therapy method that is performed in a relatively short period. Massive tumor necrosis that typically ensues after such rapid irradiation is believed to cause leukocyte diapedesis from local blood vessels due to a steep gradient of leukotaxic substances diffusing from the necrobiotic tumor mass. The large influx of leukocytes into the tumor area within a short time period will enhance tumor cell surveillance and therefore enhances the prospects of immunotherapy as compared with the slow influx of leukocytes associated with prolonged, less intensive radiotherapy.

The combination therapy of the present invention facilitates reduction in the tumoricidal radiation dosage to within a clinically tolerable range and allows more precise spatial control over the effects thereof, whereby individual cells beyond the periphery of the macroscopic tumor can be more effectively controlled. The immunotherapy can then target and be most effective against the residual tumor burdens, which should result in advantageous extension of symptom-free life.

Other objects and advantages will be in part obvious and in part pointed out more in detail hereinafter.

The present invention employs multi-modality therapy that combines a clinically tolerable dosage in radiation treatment to normal brain tissues, preferably over a short duration in conjunction with optimized immunotherapy. If appropriate and useful, the cells obtained from tumor surgery may or may not be stably transfected so that tumor clones cultured in vitro are heightened in antigenicity and different in other properties from their cells of origin. The cells cultured under sterile conditions may or may not be lethally irradiated before injection as a vaccine into the patient; they are reinjected to elicit either a heightened natural or a new iatrogenic immune response to the primary cancer cells as well as to themselves. In its preferred embodiment, this invention is implemented in conjunction with any ancillary cancer therapy that slows tumor growth e.g., antiangiogenic therapy, antisense or virosome/virus mediated gene therapy, selective enzyme-inibition therapy such as anti-PDE subtype therapy, antagonism of endogenous growth factor therapy or bacterial therapy.

The invention accordingly comprises the several steps and the relation of one or more of such steps with respect to each of the others and the products possessing the features, properties, and the relation of elements exemplified in the following detailed disclosure.

DESCRIPTION OF A PREFERRED EMBODIMENT

Figure 1:
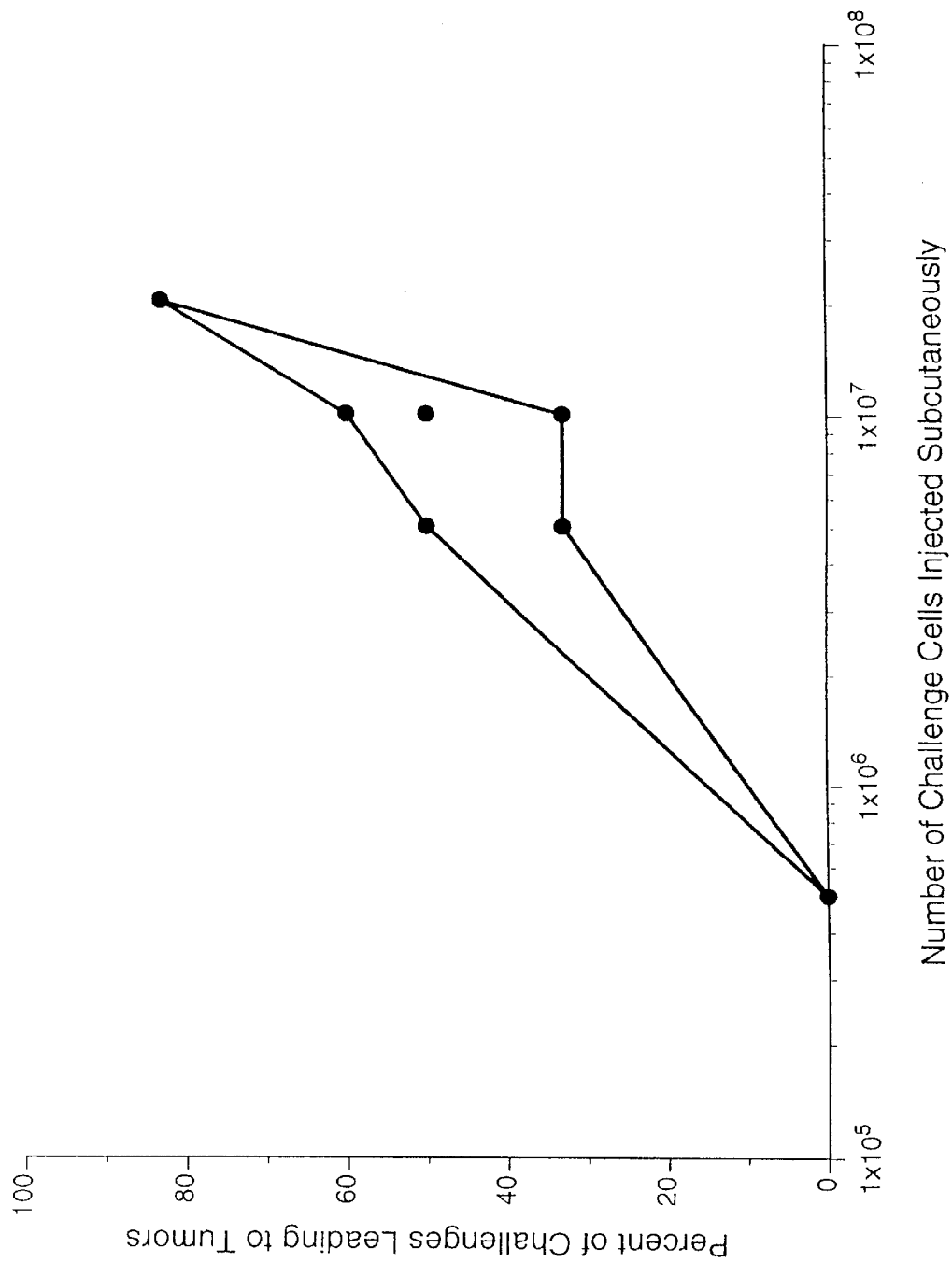
FIG. 1 is a graded-challenge-response curve showing the percent of challenges that lead to tumors as a function of the number of challenge tumor cells injected in rats receiving immunoprophylaxis with unirradiated cells.

As mentioned above, the present invention involves a method of optimizing malignancy therapy using post-operative radiation and immunotherapy techniques. It will be appreciated that certain malignant tumors may be located where surgical treatment alone or in combination with adjunct radiation or immunotherapy will provide a satisfactory result. However, it is also known that many tumors are located in an area where adjacent sensitive tissue will be placed in jeopardy by such therapies. Therefore, for purposes of illustration and ease of understanding, the invention will be described in connection with primary malignant brain tumors that are situated in or near neurologically eloquent normal brain structures. It will be understood that tumors located in extracranial areas such as those in or near the spinal cord where high levels of radiation might damage adjacent organs and tissue also will benefit from this technique.

It also will be appreciated that while the present invention envisions the surgical removal or reduction of the body burden of the malignant cells, in certain cases surgery may not be feasible or may be harmful to body functions. Then only a small portion or a mere biopsy of the tumor may be the only tissue obtainable to implement the gene-mediated immunotherapy portion of the combination treatment described herein, which would however not in any material sense vitiate the validity of this invention.

Following preliminary therapy to greatly reduce the body burden of cancer cells by surgery, radiation therapy can be implemented in the brain. The standard for conventional radiation doses, while below the thresholds for acute and delayed radiation-induced brain necrosis, typically does not take into account damage to the function and integrity of cells and tissues of the immune system. In accordance with the present invention, the radiation dosage must be such as to be below the threshold for normal tissue necrosis and, in fact, such as to provide not only for the preservation of normal tissue structure but also for maintaining and enhancing the function of tumor immunosurveillance as its prime attributes. Therapies of this type could include synchotron-generated x-ray microbeam therapy, ultra-high energy ion therapy, photodynamic therapy, conformal linac-mediated photon radiotherapy and radioisotope-mediated brachytherapy. However, the preferred technique is boron neutron-capture therapy (BNCT) because of its ability to deliver much larger doses of radiation to brain tumor cells than to the normal cells of the brain that are in the microscopically immediate vicinity of the tumor cells. The infusion of the target compound (typically, but not necessarily, enriched in boron-10) and the slow neutron irradiation can be carried out in several hours or, at most, several days and, even in its present early stage of clinical development, appears to be more or less as efficacious in tumor palliation and much less stressful to the patient than is postoperative standard radio-therapy for the most malignant kind of human brain tumors.

Ablation of those kinds of tumors, which are called glioblastoma multiforme or grade IV astrocytomas, would require at least 30 Gray (Gy) (gray: the MKS unit of physical absorbed dose representing the delivery of ionizing radiation energy to a final density of one joule per kilogram of tissue) of photon (x-ray or gamma-ray) radiation if that dose could safely be given in one session of irradiation. But a single dose of photons of that magnitude would seriously injure the normal brain, the tolerable limit being only about 12–13 Gy. In BNCT, however, the incident reactor-generated beam is a combination of sparsely-ionizing (photon) radiations with several kinds of more densely-ionizing radiations. The relative biological effectiveness (RBE) per physical dose of each reactor beam component relative to the effectiveness of its ionizing photon (x ray and/or gamma ray) components, which are set by convention to unity, is then multiplied by the physical dose attributable to that component. A special kind of RBE, compound biological effectiveness factor (CBE), is used for the boron component of the BNCT dose (Morris et al, Evaluation of CNS Toxicity to BNCT Type Irradiation Using a Rat Spinal Cord Model in Advances in Neutron Capture Therapy, Volume II, *Chemistry and Biology*, Eds. B. Larsson et al, Elsevier, 1997, pp 665–669.; Coderre and Morris, The Radiation Biology of Boron Neutron-Capture Therapy, Rad. Research, 151, p 1–18, 1999). The resulting products are added to yield the so-called "gray-equivalent" (Gy-Eq) or RBE-gray (RBE-Gy) dose used in BNCT. Thus, immune-mediated adjunct therapy will be used in synergy with BNCT which will alone deliver at least 30 Gy-Eq to tumor cells. However, even if less than 30 Gy-Eq, whether via BNCT or via any other radiotherapeutic modality, is delivered to tumor cells deep in the brain, the radiation's tumor-control efficacy should be enhanced by the adjunct cancer therapy employed.

High boron-10 levels in non-tumor brain structures are radiotoxic to normal brain tissues in large part due to damage of brain endothelial and oligodendroglial cells. BNCT requires high levels of boron-10 not only in the clonogenic tumor cells but also in normal brain structures that are microscopically contiguous with individual clonogenic tumor cells in order to kill those cells several centimeters outside the macroscopic periphery of the tumor, particularly deep in the brain. This is because the radial path lengths of the particles released in random directions following neutron capture by boron, i.e., alpha and lithium-7 particles, are ~9 and ~5 micrometers, respectively. Since the diameters of actively dividing human glioblastoma multiform (GBM) tumor cells are about 8±2 micrometers, some of the tumoricidal energy of the particles released from intracellular boron will be dissipated outside boron-10-loaded tumor cells. Therefore high levels of boron in the normal intracellular and extracellular fluids surrounding clonogenic tumor cells may be useful if not necessary if BNCT were to be the principal mode of therapy used to destroy tumor cells beyond the macroscopic periphery of the tumor. However, such high boron-10 levels in non-tumor brain structures could be toxic to normal brain tissue having neutron irradiation, especially to normal brain endothelial cells.

In general, it is believed that adult human central nervous system tissue cannot tolerate much more than 10–13 Gy or Gy-Eq of radiation in a single session to an appreciable fraction of the volume of the central nervous system without serious short-term or long-term adverse effects. There is an intrinsic limitation to the dose that can be administered to peripheral isolated clonogenic cells from any modality of BNCT which has been hitherto tested for the treatment of microscopically widely infiltrating human tumors. Thus, we believe that the method of immunotherapy described herein can be used in conjunction with BNCT or with any other kind of neutron-capture therapy (NCT) in which the dose to normal brain endothelium is raised to its tolerable maximum (probably in the range of 10–13 Gy-Eq), given to an appreciable fraction of the ipsilateral brain hemisphere's volume, while increasing the minimum dose to the brain tumor region to at least 30 Gy-Eq. Moreover, it is of great advantage to couple BNCT with an immunotherapy method that can target individual tumor cells beyond the periphery of the macroscopic tumor. Surgery and BNCT can primarily ablate the major tumor mass and then immunotherapy can primarily target the sparsely cellular microscopic nests of tumor cells beyond the periphery of the main tumor. The foregoing comments also apply to NCT and other forms of radiotherapy including NCT-enhanced fast neutron therapy and microbeam radiation therapy as well as to malignant tumors outside the brain. As clinical experience with BNCT accumulates, the numerical parameter for what are now considered ideal doses may be changed somewhat. Nevertheless, the invention would not be vitiated by any such adjustments in dose.

In its preferred embodiment, the immunotherapy should be such that the subcutaneous or intradermal injected "immunogens" stimulate the clonal expansion of therapeutically effective subsets of leukocytes, especially cytotoxic T cells, directed toward ablation of the residual cells of the neoplasm long after surgery and/or radiotherapy.

Immunotherapy will benefit from a substantial flux of immune cells throughout the targeted tumor and should be most effective with the smallest possible residual tumor burden. Immunotherapy is implemented beginning immediately after or, if appropriate, before the end of radiation therapy. In this form of immunotherapy, e.g., gene-mediated immunotherapy, cells that are genetically identical to or genetically similar to cells of the cancer being treated are cultured in vitro. Most likely, but not necessarily, they may have to be stably transfected, i.e., genetically transformed, so that the transfected cells and the progeny or clones of the transfected cells will have either membranes that are subtly different from those of their cells of origin in the patient's tumor or have biochemical properties that are subtly different from those of their cells of origin. For example, the clones may lack one or several receptors for growth factors on their surfaces or growth factors themselves or a combination of growth factors and growth factor receptors. The clones will have altered levels of molecules needed to enhance their immunogenicity and/or ability to stimulate (immune-mediated) tumor cytotoxicity. For example, these modifications will be brought about by antisense gene modification, by transfection with CD80, CD86 or MHC or by any technique found to be effective in stimulating tumor cell antigenicity. The clones are then cultivated in vitro en masse so as to provide a large number (at least several million) of identical, genetically modified tumor cells. These living cells, grown in sterile culture media, are then either used as such or processed (by supralethal doses of radiation or by other means) to render them incapable of unlimited clonogenic propagation in vitro or in vivo. Unmodified tumor cells themselves or the genetically modified tumor cells, membrane fragments of these cells, (suspended in a suitable medium, preferably with an immunogenic adjuvant, e.g., Freund's adjuvant), or specific antigenic determinants derived from those cultured tumor cells are used for injection subcutaneously, intradermally, or intramuscularly into the patient using standard sterile techniques, such injections being repeated as often as is beneficial. The whole cells or cell fragments so injected then elicit a response in the patient characterized by increased immunological surveillance and recognition of the primary cancer cells and their progeny in the patient as non-self (i.e., as foreign cell types) so as to confer to the patient an increased ability to reject, i.e., kill, any residual and/or recurrent cancer cells weeks, months, or even years after the initial therapy of the malignancy.

The present invention circumvents many of the experimental problems mentioned hereinbefore by using gene modification methods in vitro to produce gene modified tumor cells that, in conjunction with normal-tissue-sparing radiotherapy such as BNCT and the like, will stimulate, expand, and mobilize tumoricidal cells of the patient's own immune system in vivo. Additionally, this invention discloses the use of clinically relevantly-sized brain tumors experimentally, i.e., about 40 mg±20 mg tumors in the mature rat brain, occupying several percent of the test rat cranium for use in preclinical gene-mediated immunotherapy experiments in rats. The current state of the art of experimental radiation therapy generally uses rodent tumors that are considerably smaller in proportion to the size of the animal brain in which they are being tested.

A feature of this invention is that the immunological stimulation of the patient may be implemented in such a manner that the body burden of cancer cells that remains after radiotherapy is maximally subjected to immunological rejection when that burden is minimized by radiation therapy. For example, the brain tumor cells may be lethally irradiated to form after injection a transiently growing, then spontaneously regressing subcutaneous neoplasm. Alternatively, live tumor cells that intrinsically lack the biological mechanism for disseminated metastasis may be injected subcutaneously and the resulting tumors removed surgically if they do not regress spontaneously beforehand. If appropriate, the live or irradiated tumor cells may be injected in multiple microscopic jets of fluid using an apparatus similar to that known in veterinary medicine as the pig jet to maximize the efficiency with which tumor cells interact with the Langerhans cells of the lower epidermis and subcutaneous tissues which in turn will migrate as "veil" cells in the lymph to the paracortical region of lymph nodes to interdigitate with and stimulate appropriate precursors of cytotoxic T cells.

The present invention provides a combination of single-fraction or several-fraction postoperative radiation therapy with reinjection of cells or cell components derived from the patient's own brain tumor.

The tumor cells may or may not be modified by genetic transformation during cell culture in vitro and reinjected into the same patient at or shortly after the initial neurosurgical removal of the bulk of the tumor (i.e., after the first debulking). Neither of these two therapies implemented without the other will be as effective as the combination of the two because 1) radiation doses are inevitably limited by concomitant radiation damage to normal tissues and 2) the immune response to residual and regrowing tumor cells, no matter how specific, will be limited by the small fraction of the total cytocidal and natural killer T-lymphocyte population that can be not only induced to tumoricidal specificity in the human body but also induced to accumulate in and around tissues near the margins of a neurosurgical scar. There are only about one billion new lymphocytes produced per day in human adults. Thus, it is unlikely that a residual human tumor burden of more than a few percent of one billion cells could be ablated in time to prevent regrowth of a malignant brain tumor. The recently publicized developments of immunotherapy for malignant gliomas focus largely on achievement of immunospecificity in small animal tumor models, with little or no reported consideration given to quantification of the speed and intensity of an immune response in the animals that would be relevant to clinical efficacy in man. The great advantage of a single-fraction or several-fraction modality of radiotherapy, such as neutron-capture therapy or microbeam radiation therapy, is that the infiltration of radiation-sensitive lymphocytes into the surgically disturbed tissue is expected to be largely unimpeded or, at worst, delayed by several days on account of the irradiation. This infiltration is not merely desirable but essential at the earliest possible time after the debulking, although it is vitiated by the protracted postoperative course of daily radiation treatments carried out in most brain tumor therapy practiced to date. The particular kind of in vitro tumor cell transfection exemplified herein simply illustrates the kind of transfection that can be used to heighten the antigenicity of the patient's tumor cells. Likewise, the particular kind of radiotherapy employed not only is of a kind that minimally disturbs the influx of tumor-interactive leukocytes into the irradiated tissues, but also exemplifies the kinds of radiotherapy likely to induce, by themselves, such long-lasting suppression of tumor growth that there should be ample time for iatrogenic tumor-cell immune rejection reactions to take place at or near the site of previous tumor debulking, i.e., in tissues at greatest risk for tumor recurrence.

As a specific example of the invention, gene-mediated immuno-therapy of glioblastoma multiform (GBM) is implemented immediately after boron neutron-capture therapy (BNCT) or, in some cases, perhaps before BNCT but after surgical biopsy or debulking of the tumor. In the former case, on the day (or on the last day) of BNCT, one or several subcutaneous injections of the gene-modified glioblastoma cells are given to the patient. Booster injections of the same or similar immunogenic mixtures would be given at regular or irregular intervals thereafter, typically at two-week or at one-month intervals. The patient's clinical status would be assessed by a physician's direct examination of the patient and by noninvasive imaging, typically by magnetic resonance imaging, at intervals of about one month. As a result, both the length and quality of life is improved. Heightened immunological surveillance, recognition, and rejection of residual viable clonogenic GBM cells will lengthen the interval between treatment and clinically detectable recurrence as well as the interval between treatment and death from intractable overgrowth of the GBM in the brain.

The Combination of Immunoprophylaxis and Boron Neutron-Capture Therapy for Advanced Rat Brain Tumors.

After surgical reflection of the scalp, 10,000 9L gliosarcoma (9LGS) cells were injected intra-cerebrally in the left striatum about 5 mm deep to the skull and 4 mm to the left of the bregma in one microliter of culture medium under general anesthesia (Joel et al., 1989[1]; Joel et al., 1990[2]; Coderre et al., 1993[3]). Fourteen days later, when the brain tumors were expected to be about 4 mm in diameter (~40 mg), the rats were anesthetized and their tumors were irradiated at the thermal neutron port of the Brookhaven Medical Research Reactor (BMRR) for 3.15 MW-min (dosage of 40 Gy-Eq) (Day 0). The animals were infused with BPA:fructose complex in accordance with standard BNCT practice to a total dose of 1200 mg BPA/kg body weight prior to BNCT. These conditions were chosen to provide sub-optimal BNCT in which approximately ½ of the rats survive long-term (i.e.>6 months). After irradiation, one group of rats received no further treatment (BNCT only, referred to as Group 2), while another group of rats was not treated by BNCT and is used as the untreated control (Group 1). A third group of rats received a single sc injection of 5,000,000 cultured 9LGS cells into their left thighs on day 0 and the resulting tumors were excised surgically on day 11 (Group 3). A fourth group of rats received a single sc injection of 5,000,000 cultured and then irradiated (50 Gy)

9LGS cells into their left thighs on day 0 (Group 4). The fifth group of rats received a series of sc injections of 5,000,000 cultured and then irradiated (50 Gy) cells into their left thighs on days 0, 7, 21, 35, 49 (Group 5). The sixth group of rats were not treated by BNCT but were similarly injected sc with 5,000,000 cultured and irradiated cells into their left thighs (Group 6).

[1] Joel D D, Slatkin D N, Fairchild R G, Micca P, Nawrocky M M: Pharmacokinetics and tissue distribution of the sulfhydryl boranes (monomer and dimer) in glioma-bearing rats. Strahlenther. Onkol. 165: 167–170, 1989
[2] Joel D D, Fairchild R G, Laissue J A, Saraf S K, Kalef-Ezra J A, Slatkin D N: Boron neutron capture therapy of intracerebral rat gliosarcomas. Proc. Natl. Acad. Sci. USA. 87: 9808–9812, 1990
[3] Coderre J A, Makar M S, Micca P L, Nawrocky M M, Liu H B, Joel D D, Slatkin D N, Amols H I Derivations of relative biological effectiveness for the high-LET radiations produced during boron neutron capture irradiations of the 9L rat gliosarcoma in vitro and in vivo. Int. J. Radiat. Oncol. Biol. Phys. 27: 1121, 1993

Table 1 shows that none of the rats survived long-term in any group not treated by BNCT, and immunotherapy in the absence of BNCT was ineffective. The median life of group 1 was 6 days; while the median survival rate of group 6 was 5 days. Forty-three percent of the rats treated by BNCT alone survived for six months. The median survival of the BNCT-only group was 33 days. Rats treated by the combination of BNCT and a single injection of irradiated cells (Group 4) yielded 37% long-term survival. Treatment according to the present invention with BNCT and live-cell immunotherapy (Group 3) yielded 69% long-term survival; BNCT and multiple injections of irradiated cells (Group 5) yielded 80% long-term survival.

Using weight loss as an index of morbidity in the morbidity index method described by Coderre et al. 1991, addition of immunoprophylaxis (Group 3) to BNCT treatment provided the advantage of less morbidity from days 7 to 12 after BNCT (p<0.10) but not thereafter. However, addition of immunoprophylaxis in which a single sc injection of irradiated cells was used, extends that advantage from day 4 through day 28 (p<0.10) but not thereafter.

Graded Challenge Response Curve: Immunoprophylaxis with Unirradiated Cells.

Rats were injected with 5,000,000 untreated parental 9LGS cells subcutaneously (sc) in their left thigh. The resulting tumors (470 mm$^3$±92 mm$^3$) were excised surgically eleven days later. One week thereafter, the rats were challenged by contralateral sc injections with increasing numbers of untreated parental 9LGS "challenge" cells numbering 500,000 to 20,000,000. The ordinate of FIG. 1 shows the proportion of rats in which the sc injected cells formed a progressively growing neoplasm. All but one filled circle (-●-) represent six rats; one filled circle represents five rats. Whereas challenge with 500,000 cells resulted in no progressively growing tumors, challenge with 5,000,000 to 10,000,000 cells resulted in tumors in approximately half of the rats. Challenge with 20,000,000 cells resulted in tumors in 5/6 rats.

In an additional six rats, untreated 9LGS cells were first injected intradermally (id) in the ipsilateral thigh. Intradermal tumors were excised surgically eleven days later. These rats were then challenged on the contralateral side sc with 5,000,000 untreated 9LGS cells seven days thereafter. All of the resulting tumors grew progressively.

Graded Challenge Response Curve: Immunoprophylaxis with Irradiated Cells.

Figure 2:
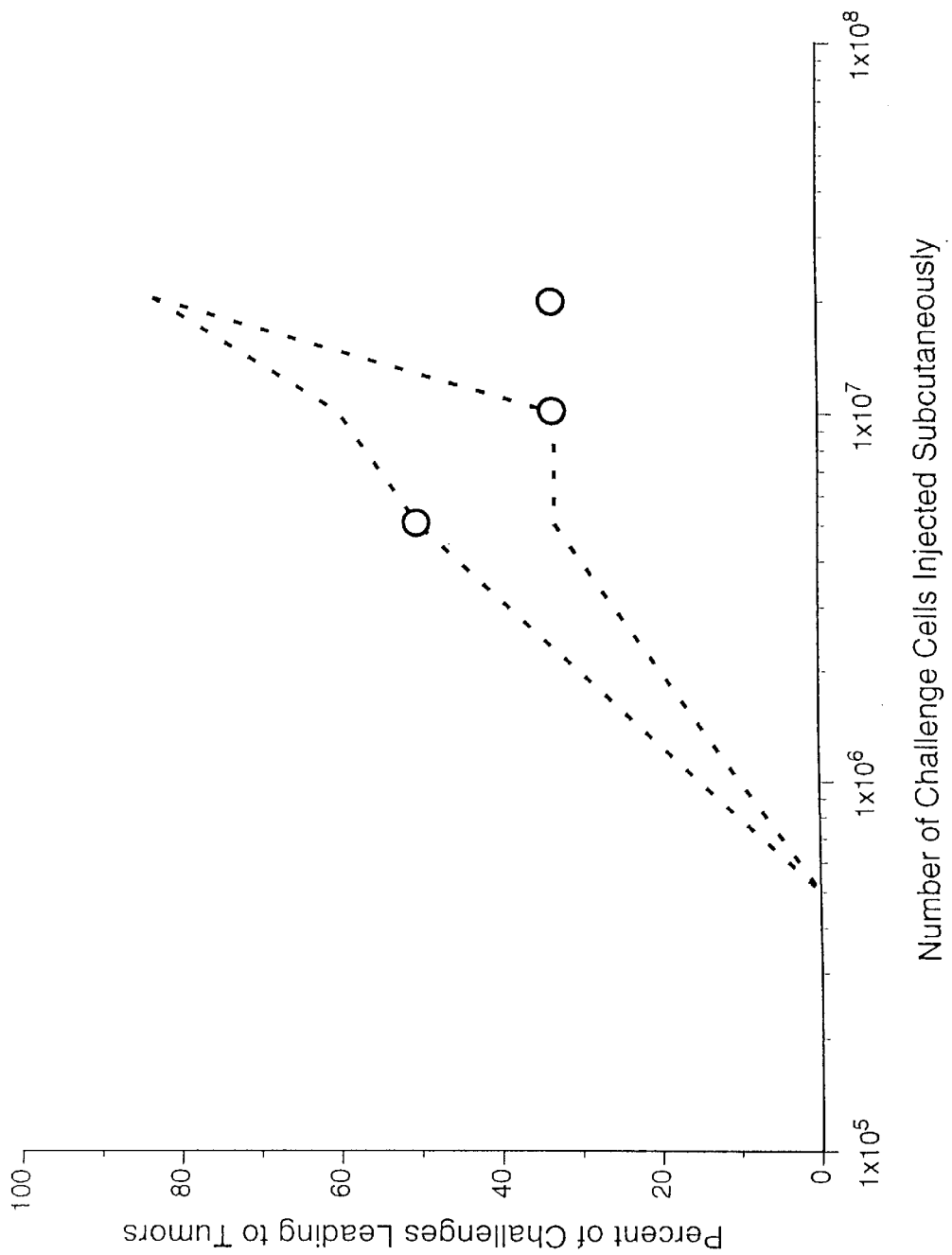
FIG. 2 is a graded-challenge-response curve showing the percent of challenges that lead to tumors as a function of the number of challenge tumor cells injected in rats receiving immunoprophylaxis with irradiated cells.

Rats were injected with 5,000,000 cultured, irradiated parental 9LGS cells (50 Gy) subcutaneously (sc) in their left thigh. Tumors were seen and palpated within three days. Those tumors disappeared spontaneously over the next week. Seven days after the first injection, the rats were injected sc in the ipsilateral thigh again with 5,000,000 irradiated cells. Similar sc injections of irradiated 9LGS cells into the left thigh of these rats were performed thereafter every two weeks. On day 18 after the first injection, the rats were injected sc (i.e. "challenged") with various numbers of untreated 9LGS cells in the contralateral (i.e. right) thigh. FIG. 2 shows the proportion of rats in which the challenge cells formed a progressively growing neoplasm at the site of injection (ordinate) as a function of the number of cells injected (abscissa). Each open circle (-o-) represents six rats. Approximately ⅓ to ½ of rats challenged with 5,000,000 to 20,000,000 untreated cells exhibited progressive tumor growth. Three open circles, superimposed on the graded challenge response curve, suggest that immunoprophylaxis with multiple sc injections of irradiated 9LGS cells (A) protects rats against a large tumor cell challenge better than (B) a single injection of live 9LGS cells and better than does (C) the surgical excision of the resulting tumor (i.e. A is better than B; A is better than C).

Those skilled in the art will recognize, or be able to ascertain using no more than routine experimentation, many equivalents to specific embodiments of the invention described specifically herein. Such equivalents are intended to be encompassed in the scope of the invention.

TABLE 1

The Combination ot Immunoprophylaxis and Boron Neutron-Capture Therapy for Advanced Rat Brain Tumors.

| Group | Number Treated | Surviving Fraction | % | Death (Days Following BNCT and Immunoprophylaxis) |
|---|---|---|---|---|
| 1 | 9 | 0/9 | 0 | days 4, 4, 6, 6, 6, 11, 11, 12, 18 |
| 2 | 21 | 9/21 | 43 | days 25, 25, 32, 33, 33, 33, 36 48, 50, 78, 95 |
| 3 | 16 | 11/16 | 69 | days 25, 26, 32, 47, 49 |
| 4 | 8 | 3/8 | 37 | days 3l, 35, 38, 47, 53 |
| 5 | 10 | 8/10 | 80 | days 22, 25 |
| 6 | 14 | 1/14 | 0 | days 4, 4, 4, 5, 5, 5, 5, 6, 6, 6, 8, 10, 10 |

Group 1: Untreated
Group 2: BNCT only
Group 3: BNCT + Single Injection of Untreated Cells
Group 4: BNCT + Single Injection of Irradiated Cells
Group 5: BNCT + Multiple Injections of Irradiated Cells
Group 6: Multiple Injections of Irradiated Cells d

What is claimed is:

1. A method of treating a malignant solid glioma in a human or animal using a multi-modality therapy, the malignant tumor defining a parental tumor strain, the therapy comprising the steps of:
   (a) surgically excising cells of the tumor;
   (b) altering said excised cells by in vitro irradiation thereby rendering said altered cells incapable of unlimited clonogenic propagation, wherein said altered cells have not been genetically modified;
   (c) subjecting the tumor to a boron neutron-capture therapy method while limiting the radiation dose received concomitantly by contiguous normal tissue to clinically tolerable levels; and
   (d) subjecting said human or animal to an immunotherapy consisting of introduction of said altered cells into said human or animal using multiple sequenced injections.

2. The treatment method of claim 1 wherein the mass of the tumor is ablated in step (a).

3. The treatment method of claim 1 wherein the radiation dose received by normal tissue adjacent the tumor is in the range of 10–13 Gy-Eq.

4. The treatment of claim 1 wherein the altered cells of step (a) are suspended in an immunogenic adjuvant suited for injection in step (c).

5. The treatment method of claim 1 wherein step (c) is implemented upon completion of step (a).

* * * * *